(12) United States Patent
Hiler, II et al.

(10) Patent No.: US 6,444,808 B2
(45) Date of Patent: *Sep. 3, 2002

(54) METHODS OF MAKING CROSS-BRIDGED MACROPOLYCYCLES

(75) Inventors: George Douglas Hiler, II, Harrison; Christopher Mark Perkins, Cincinnati, both of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/832,579

(22) Filed: Apr. 11, 2001

Related U.S. Application Data

(63) Continuation of application No. 09/380,675, filed as application No. PCT/IB98/00299 on Mar. 6, 1998, now Pat. No. 6,225,464.
(60) Provisional application No. 60/039,920, filed on Mar. 7, 1997.

(51) Int. Cl.⁷ .................... C07D 225/00; C07D 245/00; C07D 487/00; C07D 295/00
(52) U.S. Cl. .................. 540/450; 540/465; 540/470; 540/471; 540/472; 540/476; 544/247; 544/251
(58) Field of Search ................... 540/450, 471, 540/476, 465, 472, 470; 544/247, 251

(56) References Cited

U.S. PATENT DOCUMENTS 6,225,464 B1 * 5/2001 Hiler, II et al. ............. 540/450

OTHER PUBLICATIONS

Weisman et al J. Am. Chem. Soc. 112 (1990) 8604–8605.*
Weisman et al Chem. Commun. (1996) 947–948.*

* cited by examiner

*Primary Examiner*—Brenda Coleman
(74) *Attorney, Agent, or Firm*—Marianne Dressman; Kim W. Zerby; Steven W. Miller

(57) ABSTRACT

Improved synthesis of a macropolycycle, more particularly, of a cross-bridged tetraazamacrocycle.

7 Claims, 2 Drawing Sheets

METHODS OF MAKING CROSS-BRIDGED MACROPOLYCYCLES

CROSS REFERENCE TO RELATED APPLICATIONS

This is a continuation under 35 U.S.C. §120 of U.S. application Ser. No. 09/380,675, filed Sep. 7, 1999 now U.S. Pat. No. 6,225,464 of which in turn claims priority under 35 U.S.C. §371 to PCT International Application Serial No. PCT/IB98/00299, filed Mar. 6, 1998 which claims priority under 35 U.S.C. §119(e) to U.S. Provisional Application Serial No. 60/039,920, filed Mar. 7, 1997.

TECHNICAL FIELD

The present invention is in the field of macrocycle synthesis, more specifically, the synthesis of cross-bridged macrocycles having utility as proton sponges or as ligands for metal binding, especially for preparation of transition-metal containing oxidation catalysts useful, for example, in laundry detergents. The present invention is also directed to the synthesis of Mn-containing complexes of cross-bridged macrocycles.

BACKGROUND OF THE INVENTION

Whereas macrocyclic chemistry, in general, is highly developed, the art of manufacturing cross-bridged macrocycles is new. Certain such macrocycles, such as cross-bridged derivatives of cyclam, have only recently been synthesized in small amounts, and commercial processes are not known. It would be highly desirable to have such processes, since cross-bridged macrocycles have unique advantages as proton sponges or when used as ligands in the catalysis of bleaching.

Macrocycles have been made in numerous ways. See, for example, "Heterocyclic compounds: Aza-crown macrocycles", J. S. Bradshaw et. al., Wiley-Interscience, 1993, which also describes a, number of syntheses of such ligands. Though macrocycle synthesis is well developed in general, synthesis of cross-bridged macrocycles is not. Cross-bridged macrocycle synthesis is rare and difficult, and involves multiple steps and unpleasant solvents (DMF, acetonitrile, or the like).

Cross-bridging, i.e., bridging across nonadjacent nitrogens, of a known macrocycle, cyclam (1,4,8,11-tetraazacyclotetradecane), is known in limited context. It is, for example, described by Weisman et al, *J. Amer. Chem. Soc.,* (1990), 112(23), 8604–8605. More particularly, Weisman et al., *Chem. Commun.,* (1996), pp. 947–948, describe a range of assertedly new cross-bridged tetraamine ligands which are bicyclo[6.6.2], [6.5.2], and [5.5.2] systems, and their complexation to Cu(II) and Ni(II), demonstrating that the ligands coordinate the metals in a cleft. Specific complexes reported include those of the ligands 1.1:

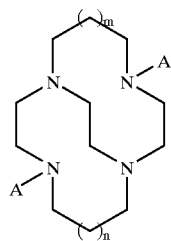

1.1 in which A is hydrogen or benzyl and (a) m=n=1; or (b) m=1 and n=0; or (c) m=n=0, including a Cu(II)chloride complex of the ligand having A=H and m=n=1; Cu(II) perchlorate complexes where A=H and m=n=1 or m=n=0; a Cu(II) chloride complex of the ligand having A=benzyl and m=n=0; and a Ni(II)bromide complex of the ligand having A=H and m=n=1. This handful of complexes appears to be the total of those known wherein the bridging is not across "adjacent" nitrogens.

Weisman also provides a synthesis method for a cross-bridged cyclam which uses three steps, two of which use acetonitrile as solvent. These steps are (1) reaction of a parent macrocycle with glyoxal to form a bisaminal and (2) quaternization of the bisaminal with methyl iodide, to form a dimethylated bisaminal diiodide. A further step, (3), reduction of the diquaternary intermediate produced in the second step, is required to make the desired product. This step uses ethanol as solvent. There is an apparent requirement to conduct the synthesis at relatively high dilution, which is commercially unattractive. Yields are borderline for commercial utility ( only 80% and 85% in the first and second steps, respectively.) In view of the desirable properties of cross-bridged macrocycles as ligands and the limitations of the existing method of making such a macrocycle, there is a clear need and desire for improvement in the synthesis of such cross-bridged macrocycles.

To summarize, current syntheses have one or more of the following limitations: (a) they use relatively environmentally undesirable solvents, such as acetonitrile; (b) they may incorporate "high-dilution" steps, increasing solvent consumption; (c) they require switching from one solvent to another in different stages of manufacture; increasing cost and complexity further, and (d) they are wasteful in calling for large excesses of materials such as alkyl halides and/or reducing agents.

Accordingly, it would be highly desirable to improve the synthesis of cross-bridged macrocycles, and in particular, methods for making cross-bridged derivatives of cyclam, and to provide methods for synthesizing Mn-containing complexes with cross-bridged macrocyclic ligands. These and other improvements are secured herein, as will be seen from the following disclosure.

BACKGROUND ART

See documents cited in the background. Also, Tabushi and co-workers, cited in Bradshaw et al., supra, make use of ethanol as a solvent for preparing a tetraazamacrocycle by dimerization. However, the macrocycle is not cross-bridged and the method described is not capable of forming a cross-bridged macrocycle.

SUMMARY OF THE INVENTION

Figure 1:
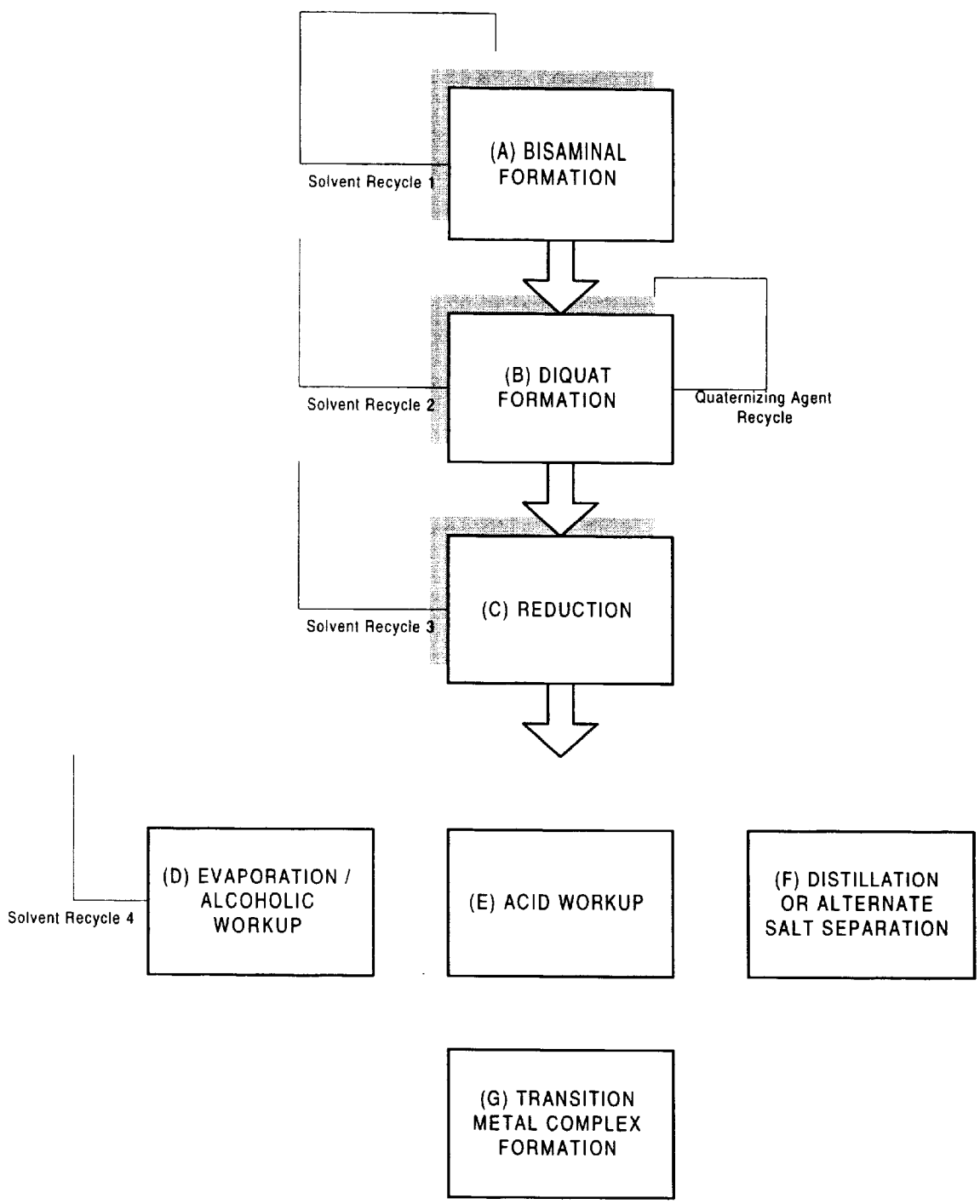
FIG. 1 is a process outline presented for purposes of orienting in the present process. In a preferred embodiment, the present process has a series of essential steps, marked (A), (B), and (C) in FIG. 1; these are single steps, they are marked in bold, and they are conducted in sequence. The process may also contain further operations, such as (D), (E) or (F), any one of which operations may comprise one or more steps and which may be used to work up the crude product of the essential process steps; the product may then be sold or used for further conversions, for example in one or more steps to make a useful transition-metal bleach catalyst (G). The process desirably incorporates solvent recycle from one or more of (A), (B), (C) and (when used), (D).

In one aspect, the present invention relates to a method for preparing a cross-bridged macropolycycle, preferably a cross-bridged tetraazamacrocycle, comprising a series of steps, preferably three steps in sequence, of derivatizing cyclam or a particular acyclic tetraamine, wherein said series of steps is carried out using in common in each of said steps, substantially one solvent system. Preferably, said solvent system is an alcoholic solvent system; more preferably the solvent system comprises from about 60% to 100% of a C1–C4 alcohol, such as methanol, ethanol, n-propanol, 2-propanol, n-butanol, t-butanol, or mixtures thereof; ethanol and 2-propanol are preferred. More generally, and in preferred embodiments, mixtures of lower alcohol and, for example, from about 0.1% to about 70% water, more typically from about 1% to about 40% water, can also be useful and economic. In a highly preferred embodiment, said solvent system is substantially ethanol or mixtures thereof with water. The solvent system is preferably completely free from acetonitrile. Accordingly, the invention secures a "one-pot" method for making the cross-bridged macrocycle. "One pot" methods in general are highly advantageous—they permit reduced investment in manufacturing steps and equipment. Such an advantage is secured by the present process, which is simple, economic, and improved in terms of environmental acceptability.

The invention further relates to a method for preparing a cross-bridged macropolycycle comprising a series of steps of derivatizing cyclam or a particular acyclic tetraamine including a step of quaternizing an intermediate using a quaternizing agent, wherein said step is carried out using a minimized amount of said quaternizing agent.

The invention further relates to a method for preparing a cross-bridged macropolycycle comprising an alternate first step of forming a bisaminal by (i) reacting a suitable acyclic tetraamine with glyoxal to form a tricyclic macropolycycle and (ii) converting the tricyclic compound to the bisaminal by reacting it with a dihaloalkane, preferably and more generally a compound selected from the group consisting of $\alpha,\omega$-dichloroalkanes, $\alpha,\omega$-dibromooalkanes, $\alpha,\omega$-diiodoalkanes, $\alpha,\omega$-ditosylalkanes and mixtures thereof, more preferably $\alpha,\omega$-dibromooalkanes or $\alpha,\omega$-ditosylalkanes.

Preferably, the method of the invention has a second step which is carried out using less than about fifteen-fold of said quaternizing agent; typically, levels of about five-fold to about 10-fold of said quaternizing agent can be practiced. "Reagents" herein are materials, such as the glyoxal of step A, the quaternizing agent of step B, or the reducing agent of step C, which are chemically reacted with a macrocycle. Ratios of reagents herein, unless otherwise noted, are expressed on a molar basis; thus the term "three-fold" with respect to an amount of reagent over an amount of macrocycle means that the amount of reagent is three times the number of moles of the macrocycle it is being used to functionalize. A suitable quaternizing agent is methyl iodide, but the present method contains the further improvement of providing alternative, more environmentally attractive quaternizing agents further illustrated hereinafter.

In another aspect, the present invention encompasses a method for preparing a ross-bridged macropolycycle comprising a series of steps of derivatizing cyclam or a particular acyclic tetraamine including a step of reducing a diquaternized intermediate, herein said step is carried out using a minimized amount of reducing agent. Preferably, said step is carried out using an amount of less than about fifteen-fold of said reducing agent. More typically, the reducing agent is from about 2.5- fold to about 10-fold the amount of macrocycle, on a molar basis.

In general, any suitable reducing agent, both catalytic and non-catalytic, may be used. For example, a tube reactor containing materials for catalytic hydrogenation providing a locally high concentration of reducing species can be used. Alternately, a preferred group of reducing agents herein, especially for the one-pot process, are non-catalytic reducing agents. For example Zn/HCI is a well-known reducing agent having the advantage that it can be used in water, and can be used herein. Preferred non-catalytic reducing agents are hydride compounds; more preferred are hydride compounds which can be used in wet (water-containing) systems. Preferred hydride compounds are borohydride and borane. Suitable borohydride compounds are selected from sodium borohydride and potassium borohydride. Less preferably, lithium borohydride can be used. When using borohydrides in methanol or ethanol herein, pH may be adjusted using small amounts of alkali to limit wasteful decomposition and release of hydrogen from the hydride. 2-propanol and t-butanol have known advantages of producing less wasteful hydrogen evolution than, say, methanol or ethanol.

The invention also encompasses a method in which sodium ion is substantially absent. The terms "substantially absent" or "substantially free" in connection with a material herein mean that the material is not deliberately added, though adventitious amounts are permissible. Surprisingly, sodium ion, though usable, has some adverse effect on the method, so sodium ion, other than adventitious amounts, are excluded in certain preferred embodiments.

Although the invention overall is not so limited, in a further aspect, the present invention relates to a method having each of the foregoing steps, in sequence. As noted, the steps can be carried out in "one pot" to secure the maximum advantages. Of course, the practitioner may choose not to secure the maximum benefits, for example if the different steps are carried out at multiple manufacturing locations, or for other reasons, such as a desire to use a specialized hydrogenation reactor in the third step. In this instance, practitioners may still avail themselves of the improvements in any one or two of the individual steps in any one manufacturing location or facility.

In preferred embodiments, the invention further relates to the method described hereinabove which is carried out in the absence of any step of vacuum distilling an intermediate; and to a method which is carried out at low temperatures, especially wherein said quaternization and reduction steps are carried out at the low temperatures of from about ambient temperature to about 50° C., more preferably lower than about 50° C.

In preferred embodiments, all steps are carried out at concentrations of the reactants of about 7% or higher, by weight in total of the sum of reactants plus solvent; preferably, the concentrations of the reactants exceeds about 15% in total of the sum of reactants plus solvent. This permits the use of smaller and less costly manufacturing plant and the use of lower, safer amounts of flammable materials.

As will already be apparent, the invention secures numerous advantages in relation to the manufacture of cross-bridged macrocycles, as non-limitingly illustrated by cross-bridged cyclam derivatives. Indeed the advantages of the present method make a substantial difference to the possibility of commercially producing cross-bridged macrocycles for the useful purposes outlined in the background.

Finally, the present invention relates to a method for producing a complex of Mn with a cross-bridged macrocyclic ligand. Said method comprises preparing said complex, preferably under strictly oxygen and hydroxyl-free (ideally completely anhydrous) conditions by reaction of $MnCl_2$ with a cross-bridged macropolycycle.

All ratios, proportions and percentages are by weight unless otherwise specifically indicated. An exception is yields. Yields are given as percentages obtained of the amounts expected for complete chemical reaction according to the equations given. Percentage yields can, of course, be computed on either a weight or a mole basis, given the designated reactions.

DETAILED DESCRIPTION OF THE INVENTION

In a preferred embodiment, the present invention involves a process or method having three essential steps, (A), (B) and (C) as shown in FIG. 1, optionally followed by additional steps. In one such embodiment,
Step A is non-limitingly illustrated as follows:

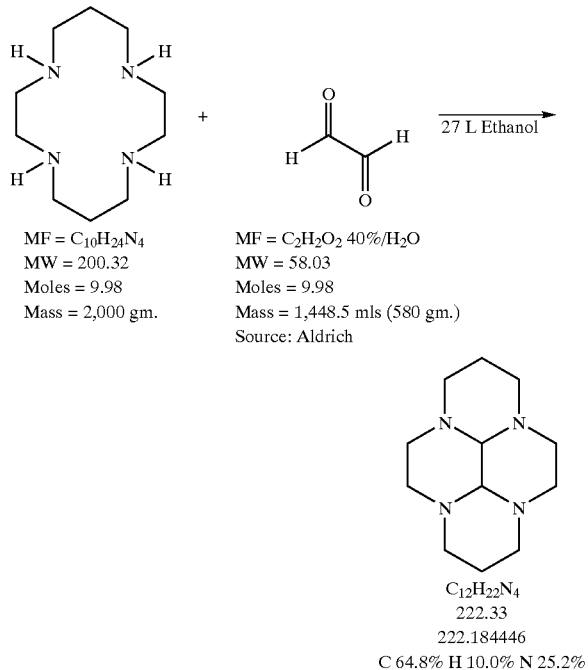

The above step, the yield of which is from about 85% to 100%, typically near quantitative (100%), can be carried out using ethanol as a solvent and a concentration of reactants of 7%. The reagent, glyoxal, can be used pure or undiluted, or as a solution, for example and aqueous solution. More generally, in this step, the concentration of reactants by weight in the sum of all solvents including water, if present, is in the range from about 7% to about 20%, or higher. Thus, cyclam is slurried at 7% in ethanol. The slurry is stirred using any convenient stirring means, such as a mechanically driven paddle stirrer. The above depicted co-reactant, glyoxal, is dripped in, preferably keeping the temperature below about 35° C. More generally, the temperature can be in the range from about 10° C. to about 40° C. After the addition reaction is over, typically within one hour, more generally in from about 10 min. to about 3 hours, it is found to be quantitative by any suitable means, for example C-13 NMR. Step (A) and all other steps herein can in general be conducted at atmospheric pressure, or overpressures if desired. The term "overpressures" herein means pressures greater than atmospheric. Although preferred embodiments of the invention include those conducted at atmospheric pressure, any step or steps can be conducted at overpressures, for example to contain volatile solvents or reagents above their normal boiling-points. The cis-tetracycle (product of step (A)) is not isolated; rather it is kept in the reaction solvent and the process proceeds to step (B).

In another preferred embodiment, the cis-tetracycle is prepared using the following scheme:

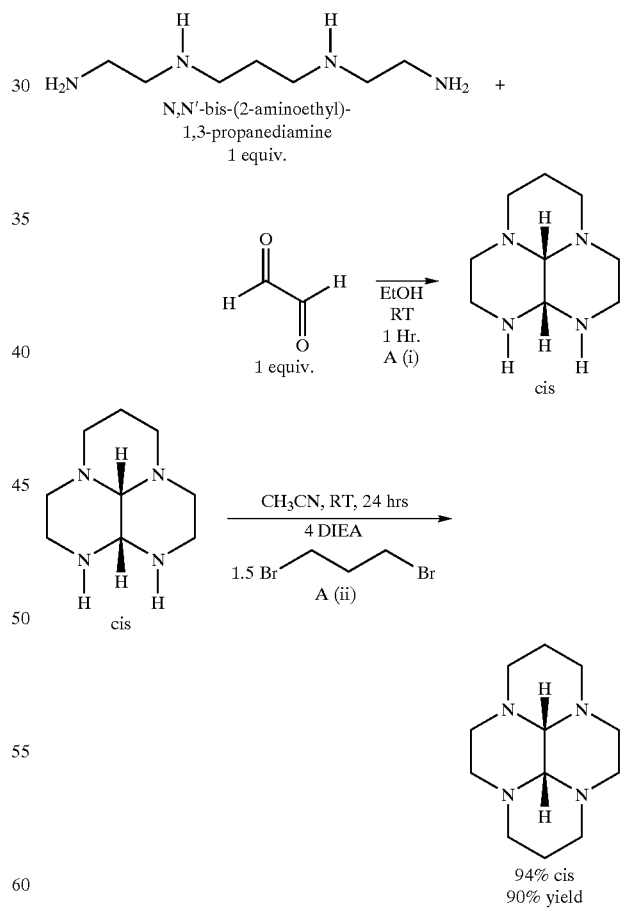

This alternate procedure is referred to as alternate Step (A), comprising step A(i) and step A(ii) as shown. In more detail, a suitable tetramine, N,N'-bis-(2-aminoethyl)-1,3-propanediamine, is reacted with glyoxal, typically about 1–10 molar equivalents, preferably from about 0.8 to about 1.5 molar equivalents, very suitably 1 molar equivalent, in a solvent, ethanol being preferred, at temperatures in the range from about 0 to 100° C., more preferably 0 to 25° C., for a period of from about 1 min. to about 7 days, preferably from about 15 min. to about 2 hours. The intermediate product, a tricycle of the shown structure, can either be isolated by distillation or can be further reacted to form the cis-tetracycle without changing reactor. The conversion of the tricycle to the cis-tetracycle can suitably be conducted using a 1,3-dihalopropane, typically 1,3-dibromopropane, or the ditosylate of 1,3-propanediol can alternatively be used. Suitable solvents are ethanol (ideal for one-pot purposes) or acetonitrile. A base is used to prevent the tricyclic amine reactant from protonating as the reaction continues. Suitable bases can vary widely and can include potassium carbonate or organic bases which are resistant to alkylation, such as di-isopropylethylamine (Koenig's base). The amount of the base is typically from 1–10 equivalents, preferably from about 2 equivalents to about 6 equivalents. The reaction temperature is in the range from about 0 to 100° C., more preferably 0 to 30° C., for a period of from about 15 min. to about 7 days, preferably from about 30 min. to about 2 hours. Depending on the base used, workup can vary. With potassium carbonate, for example, the reaction mixture is filtered to remove solid base and the filtrate is evaporated to yield the cis-tetracycle as a solid. With an organic base, the solvent is evaporated and the evaporate is distilled. Step (B) is non-limitingly illustrated as follows:

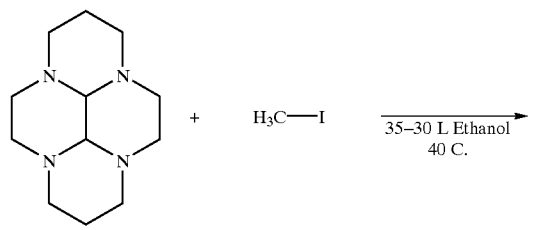

MF = C$_{12}$H$_{22}$N$_4$
MW = 222.33
Moles = 9.98
Mass = 2,215 gm.

MF = CH$_3$I
MW = 141.93
Moles = 59.88
Mass = 8500 gm
Source: Aldrich

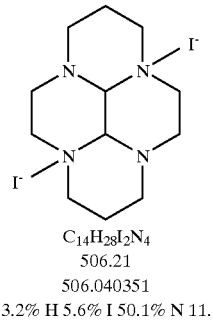

C$_{14}$H$_{28}$I$_2$N$_4$
506.21
506.040351
C 33.2% H 5.6% I 50.1% N 11.1%

After making the cis tetracycle (product of any variation of step(A)), this material is quaternized, as non-limitingly illustrated using alkyl halide (CH$_3$I) in the reaction scheme. Such a step has a yield of about 80%, or higher. Yields of 80% can typically be achieved. More generally, in this step, the concentration of reactants by weight in the sum of all solvents including water, if present, is in the range from about 7% to about 20%, or higher. In a preferred embodiment, from about 2.01 to about 14 equivalents, preferably from about 2.5 to about 8 equivalents, for example 7 equivalents of methyl iodide are added to the reaction solution and the reaction is stirred using any convenient means, such as a mechanically driven stirrer (sparkless motor). More generally, any one or more alkyl halides can be used, for example a mixture of methyl iodide and 1-iodopropane. As will be seen from the working examples hereinafter, by introducing a second alkyl halide in addition to methyl iodide, step (B) is thereby modified to allow access to additional macrocyclic compounds as alternate products of the present process. The temperature is maintained in the general range from about 10° C. to about 38° C., more preferably from about 15° C. to about 30° C. At the low end of these reaction temperatures, there is a tendency for more monoquaternized intermediate (not shown in the reaction sequence) to precipitate. At the high end of these reaction temperatures, there is more tendency to form undesired byproducts, such as a triquaternized derivative (also not shown in the reaction sequence). Desirably, in view of byproduct formation tendencies, mono-quat intermediate is precipitated; but in order to maximize reaction rate, measures are taken to keep the particle size small and the surface area of intermediate mono-quat as high as possible. Vigorous stirring, small adjustments of the solvent system, or compatible additives, for example inert water-soluble nonsodium salts, can help. Illustrative of reaction time in step (B) is a period of from about 0.5 hours to 72 hours. Typical reaction times when not taking any special measures to accelerate reaction are from about 24 hours to about 72 hours, for example about 48 hours. The monoquat intermediate referred to supra usually begins to separate from solution about 1 hour after addition of methyl iodide. The reaction can desirably be monitored, for example by C-13 NMR. When reaction to form diquat is complete the ethanol can, if desired, be siphoned off (this is convenient, especially for the one-pot variation of the present process). Solvents are desirably recycled in this and all other steps where recycle is possible. Recycle can be by any convenient means, for example by means of conventional distillation apparatus. Solid product of step (B) can be washed with ethanol, typically several times, to remove excess methyl iodide. Step (B) can be conducted at atmospheric pressure; however, any suitable overpressure may be quite desirable when the quaternizing agent is low-boiling.

Other alkyl halides, such as chloromethane, or, more generally, other quaternizing agents such as dimethyl sulfate or methyltosylate, can be substituted in the above procedure. As noted, faster reaction times occur when the mono-quat is solubilized, but faster reaction times, for example using dimethyl sulfate/water/ethanol, may increase tendency to form an undesired tri-quat.

As noted, the desired product of this step, the di-quat compound shown in the illustration, is derived from an initially-formed and practically insoluble mono quat. Note that in relative terms, the di-quat compound is even more insoluble than the mono-quat. In order to accelerate the reaction, it might have been thought desirable to solublize the mono-quat; however, excessive solubilization of mono-quat intermediate, which, in turn, may lead to undesirable solubilization of diquat, is avoided in preferred embodiments of the present process, thereby limiting formation of undesired, tri quat byproduct.

Step (C) is non-limitingly illustrated as follows:

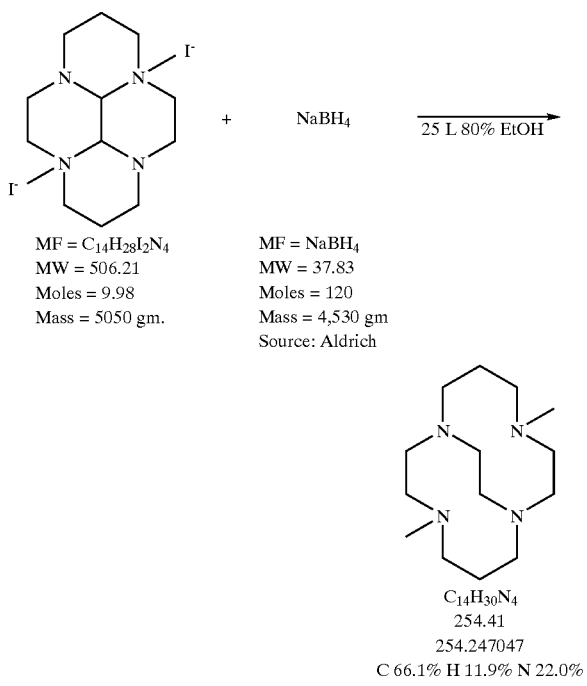

MF = C$_{14}$H$_{28}$I$_2$N$_4$
MW = 506.21
Moles = 9.98
Mass = 5050 gm.

MF = NaBH$_4$
MW = 37.83
Moles = 120
Mass = 4,530 gm
Source: Aldrich

C$_{14}$H$_{30}$N$_4$
254.41
254.247047
C 66.1% H 11.9% N 22.0%

Step (C) is a reduction step, having typical yield of 80% or higher. The solids from the diquat reaction of step (B) are dissolved in water and ethanol is added to make a 80% ethanol solution; the final concentration of the diquat is 20% by weight in the total of solvents (for example 81:19 ethanol:water by weight). More generally, C1–C4 lower alcohol may be used in all of steps (A), (B) and (C) and in step (C) a preferred solvent system comprises from about 50% to about 95% lower alcohol and the balance water. An excess, preferably from about 3 to about 10, for example, 6, equivalents of sodium borohydride are added slowly, with stirring using any convenient means. For convenience, the borohydride may, for example, by slurried in a portion of solvent and added as the slurry, if it is desired to avoid solids-handling and obtain excellent control of the addition. On addition of the borohydride, the reaction becomes very exothermic. Temperature is maintained in the range from about 0° C. to about 80° C., more preferably from about 20° C. to about 50°, using cooling means such as an ice bath if needed. Once all borohydride is added, the reaction mixture is stirred, generally from about 1.5–72 hours, typically up to ethanol reflux. Longer reaction times at relatively lower temperatures are safest in this step (C) and safety may be further enhanced by passage of an inert gas, such as nitrogen, to flush out hydrogen, especially from the reactor headspace. Suitable reducing agents herein include the borohydrides, but preferably, non-sodium salt forms. Reaction is optionally monitored by ion spray mass spec. This constitutes the end of the basic process: it will be seen that all the above has been accomplished using ethanol or equivalent lower alkanol (preferably with some water) as the solvent. The crude product is useful as an intermediate for further processing as illustrated herein.

Steps (D)–(G)

Figure 2:
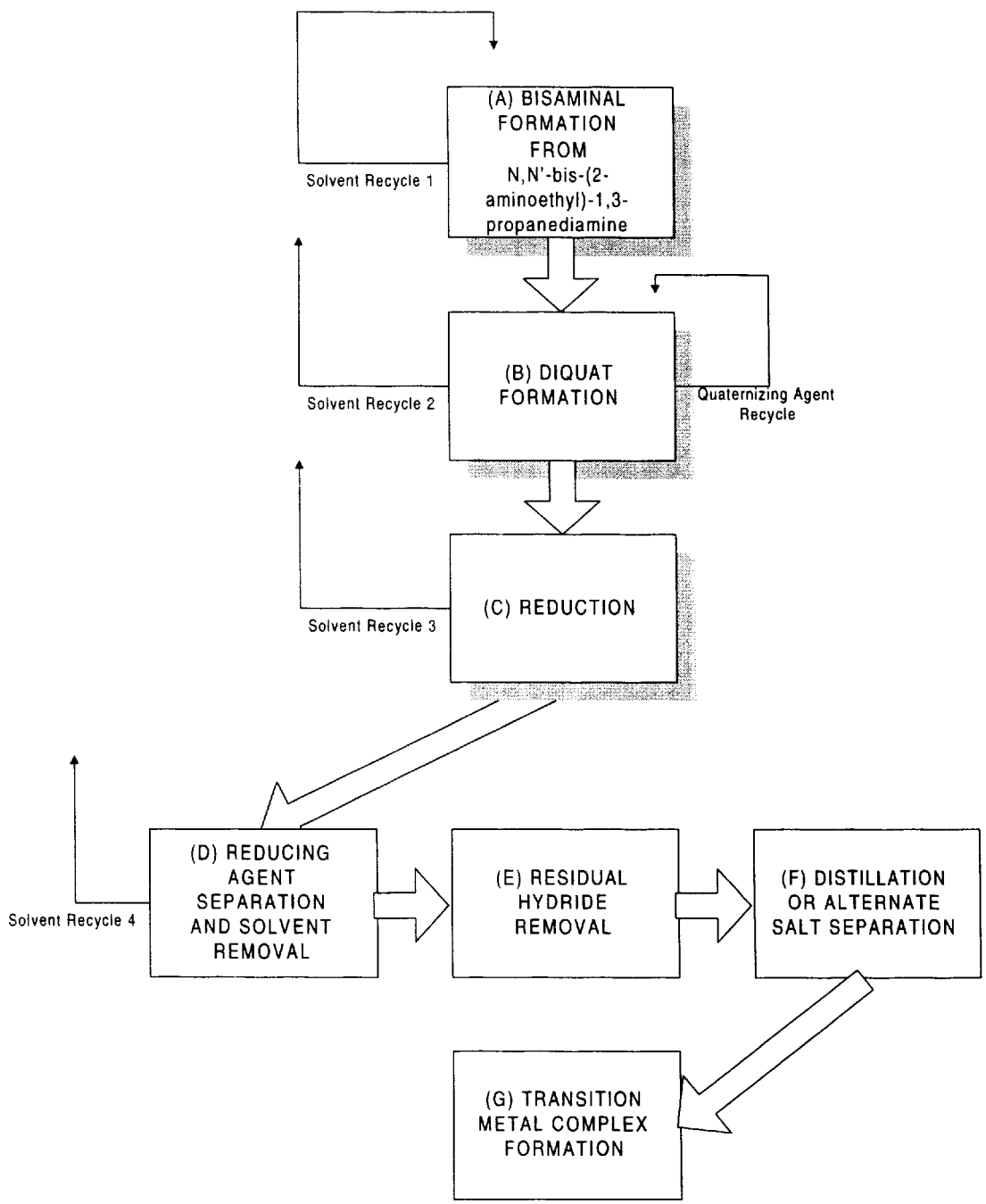
FIG. 2 is also a process outline for a preferred embodiment of the invention. In this process, the bisaminal in step (A) is formed from a relatively inexpensive acyclic amine. In step (B) the bisaminal is converted to a specific diquatemary derivative. In step (C) this is reduced. In step (D), reducing agent and solvent are separated in one or more separation operations. In step (E), which in general is optional but is preferred if there is any appreciable amount of reducing agent left after step D, residual hydride is removed. In step (F) the product, a cross-bridged macrocycle suitable for forming transition metal complexes which are useful bleach catalysts in detergents, is isolated. In step (G) optionally including one or more purification steps on the final product, transition metal complex of the cross-bridged macrocycle is formed. (A)–(G) occur in the indicated sequence.

As can be seen from FIG. 1 and further illustrated in FIG. 2, any of a range of alternative steps or combination of steps may follow step (C). For example, once the step (C) reaction is finished, a step identified as (E) in FIG. 1. can be used. In such a step, the pH is adjusted to between 1 and 2 with 37% HCl (slow addition of acid is required, reaction is very exothermic) and the reaction solution is concentrated at reduced pressure to a thick slurry. The thick slurry is then made basic (pH>14), for example with 8M KOH. If desired, product can be extracted with toluene and subjected to further purification, such as by distillation. Preferred embodiments of the instant invention, however, include those not having vacuum distillation as a requirement.

An alternative procedure for workup, (D) in FIG. 1, simply involves evaporating to dryness the crude product of step (C); the organic product is then separated from residual salts by extraction with ethanol. Another alternative workup, (F), is illustrated by a direct distillation of the desired product from the crude reaction mixture. The product can then be used for conversion to useful transition-metal complexes, especially the dichloro-Mn(II) complex, which are effective bleach catalysts, preferably by the present invention process by reaction with MnCl$_2$.

In more detail, with reference to FIG. 2, a preferred workup sequence comprises the steps of (D) (i) reducing agent removal, for example by simple filtration, (D) (ii) solvent removal, for example by evaporation, (E) residual hydride removal, for example by using acid-treatment followed by base treatment as defined supra, and (F) separation of the desired cross-bridged macrocycle, for example by distillation. The product of step (F) is used in subsequent step (G) to form a transition-metal complex, for example a complex of manganese.

A preferred product of the present process (product of step (C)), is 5,12-dimethyl-1,5,8,12-tetraaza-bicyclo[6.6.2] hexadecane. This product is obtained when cyclam is used as the parent macrocycle. However, the invention methods should not be taken as limited to this particular material, as it is equally amenable to the preparation of any one of a wide range of cross-bridged macrocycles. For example, any one or more substituent moieties such as alkyl or alkaryl moieties, may be present, covalently attached to the parent macrocycle used in step (A). Moreover, other macrocycles can be made by the process through the variation of adding methyl halide along with another alkyl halide in step (B). Thus, for example, 5-n-butyl-12-methyl-1,5,8,1 2-tetraaza-bicyclo[6.6.2]hexadecane can be prepared by the present process by use of a mixture of 1-iodobutane and methyl iodide, very preferably by consecutive reaction first of an equivalent of iodobutane then an equivalent of methyl iodide, in step (B). Similarly, the present process can be used to prepare the cross-bridged macrocycle 5-benzyl-12-methyl-1,5,8,12-tetraaza-bicyclo[6.6.2]hexadecane, simply by use of the variation of adding methyl iodide and benzyl bromide, instead of only methyl iodide, in step (B). All of these cross-bridged macrocycles can thus be prepared using the desirable features of the invention, for example their independence from use of dimethylformamide or acetonitrile and their improved yields, especially in step (A), all to great economic advantage.

In a preferred embodiment of the present invention, the macrocyclic ligand is reacted directly with manganese as an inorganic salt free of organic ligands such as pyridine, to form useful transition-metal complexes. The source of manganese chloride can include analytical and technical grades, and can be fully anhydrous or only partly anhydrous. Manganese chloride is commercially available from Chemetals Corp., Spectrum Bulk Chemicals Corp., American International Chemical Inc., Barker Industries Inc., and Mineral Research and Development Corp. As noted in Kirk-Othmer's Encyclopedia, manganese chloride can be prepared from the carbonate or oxide by dissolving it in hydrochloric acid. Heavy-metal contamination can be removed by precipitation through the addition of manganese carbonate which increases the pH. Following filtration, the solution can be concentrated and upon cooling, crystals of $MnCl_2 \cdot 4H_2O$ are collected. If an anhydrous product is desired, dehydration in a rotary dryer to a final temperature of 220° C. is required. Anhydrous manganese chloride can also be made by reaction of manganese metal, carbonate or oxide, and dry hydrochloric acid. Manganese chloride is manufactured by Chemetals Corp., using a process in which manganese(II) oxide is leached with hydrochloric acid. Manganese carbonate is added after completion of the initial reaction to precipitate the heavy-metal impurities. Following filtration of the impurities, the solution is concentrated and cooled and the manganese chloride is isolated. Gradual heating in a rotary dryer above 200° C. gives anhydrous manganese chloride. For top quality $MnCl_2 \cdot xH_2O$ grades, the starting-material is manganese metal or high purity MnO. To make anhydrous $MnCl_2$ directly, manganese metal or ferromanganese is chlorinated at 700° C. to 1000° C. Any iron trichloride initially present in the product is removed by sublimation. For more detail on manganese chloride, see Kirk Othmer's Encyclopedia of Chemical Technology, 4th Ed., Wiley, 1991, "Manganese Compounds", pp 991 and following. It is an advantage of the present invention to be able to proceed all the way from step (A) to step (G) (see FIG. 1) without having to make an intermediate complex of manganese with an organic ligand. Moreover, although high-purity manganese chloride grades, especially those which are totally anhydrous, work very well in the instant invention, it is a further advantage to be able to use grades such as the 98%+ grade and the 99% grade which are not totally anhydrous and are available at substantially lower cost. On the other hand, for the most exacting purity, it can be desirable and is equally encompassed herein to use a manganese chloride which has been made by the anhydrous route from the pure metal.

The macropolycyclic ligands herein (product of step (C)) can be reacted with manganese chloride in any convenient manner. See Examples 10 and 11, in each, see (b), Method (II). Any variation of such non-limiting illustrations of the process for step (G) of the instant invention are encompassed herein; for example, argon or nitrogen and degassing procedures while they can be useful for best results can be dispensed with, especially in larger-scale commercial operation; likewise rotary evaporation and other laboratory-scale procedures can readily be scaled up to commercial-scale equipment. Any convenient organic solvent can be used, for example acetonitrile, though other solvents are also possible. Typically the step (G) conversion of macrocyclic ligand to transition-metal complex is conducted at temperatures from about ambient to about 100° C., preferably from about 40° C. to about 80° C.; and no water is deliberately added to the solvent system. Pressures are typically atmospheric, though higher pressures may be used if desired, for example to help contain volatile solvents.

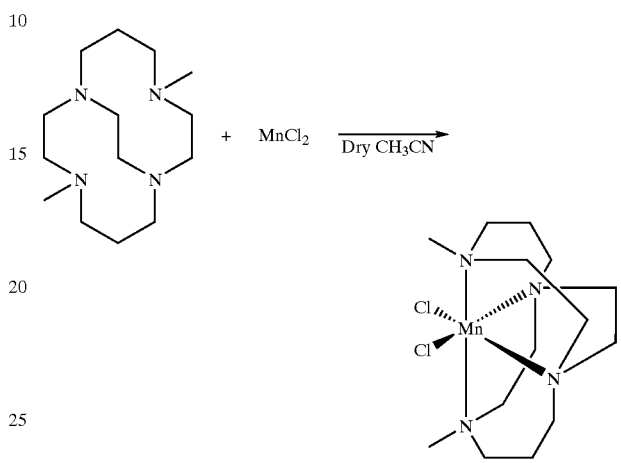

The present invention is further non-limitingly illustrated by the following examples.

EXAMPLE 1

The method of the invention illustrated by steps (A)+(B)+(C) as described in detail hereinabove is carried out using the following parameters:

Step A Reagents: Parent macrocycle, MW 506.21, 10 moles
Step B reagents: Product of step A and Methyl Iodide
Step C reagents: Product of Step B and Sodium Borohydride.

All steps are conducted in a single reaction vessel equipped with a mechanical stirrer and means for gas inlet and outlet. Purging of hydrogen is accomplished using nitrogen or argon.

| | Press. (atm.) | Temp (° C.) | Time (hrs.) | Reagent (mole ratio to macrocycle) | Total Reagent concentration (%) | Solvent |
|---|---|---|---|---|---|---|
| Step (A) | 1 | 30 | 1 | 1:1 | 7 | Ethanol/Water (97:3 vol.)* |
| Step (B) | 1 | 38 | 48 | 6:1 | 7 | Solvent of Step A |
| Step (C) | 1 | 40 | 24 | 6:1 | 20% | Ethanol/Water (80:20 vol.)* |
| Alternate Step (C) | 1 | 78 | 2 | 4:1 | 20% | Ethanol/Water (80:20 vol.)* |

*Using known densities, these volume ratios, provided for convenient handling of materials, can readily be converted to weight ratios in accordance with preferred weight ratios cited elsewhere herein.

EXAMPLE 2

The method of Example 1 is repeated, except that an equal number of moles of dimethylsulfate replaces the methyl iodide.

EXAMPLE 3

The method of Example 1 is repeated, except that potassium borohydride replaces sodium borohydride in equimolar amount.

EXAMPLE 4

The method of Example 1 is repeated, except that the solvent system is ethanol-only in steps A and B.

EXAMPLE 5

The method of Example 1 is repeated, except that the solvent system is substantially water.

EXAMPLE 6

The method of Example 1 is repeated, except that steps A and B are carried out in the original reaction vessel while step C is conducted in a second reaction vessel. The first reaction vessel is then freed from the requirement to handle hydrogen evolution.

EXAMPLE 7

The method of Example 1 is repeated, except that the reagent ratio to macrocycle is 1.1-fold, 3-fold and 3-fold in steps (A), (B) and (C) respectively. (In the terms given in the Table of Example 1, column 5 numbers are 1.1:1, 3:1 and 3:1). In another variation, a mixture of methyl iodide and 1-iodobutane replaces the methyl iodide of Example 1, demonstrating that the present process can be used to prepare different kinds of cross-bridged macrocycles.

EXAMPLE 8

Purification of the product of Example 1. (Conventional). Aqueous phase crude product from Example 1 is extracted with 5 portions of toluene. The extracts are combined and evaporated. The product is vacuum distilled at 100° C., 0.1 mm Hg.

EXAMPLE 9

This example further illustrates the conversion of product of Example 1, after purification, to a useful bleach catalyst by the present invention process.

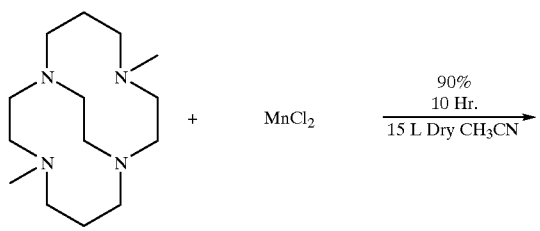

MF = $C_{14}H_{30}N_4$
MW = 254.41
Moles = 5.99
Mass = 1520 gm.

MF = $MnCl_2$
MW = 125.84
Moles = 5.6
Mass = 704.7 gm
Source: Aldrich

90%
10 Hr.
15 L Dry $CH_3CN$

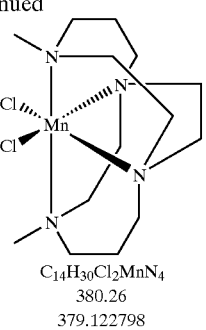

$C_{14}H_{30}Cl_2MnN_4$
380.26
379.122798
C 44.2% H 8.0% Cl 18.6% Mn 14.4% N 14.7%

Reagents according to the present invention are in anhydrous form. Product of Example 1 after conventional purification (for example distillation) is slurried in a 10% solution of acetonitrile and degassed with argon. Anhydrous $MnCl_2$ (more economically, 98% or 99% grade) is then added and the reaction refluxed under argon for 4 hours. Reaction can be monitored qualitatively by color; pale blue being positive indication reaction is proceeding normally—any ingress of air may cause darkening. The reaction mixture is then filtered hot through a glass micro fiber filter and, if desired, again through a 0.2 micron filter. Filtrate is then concentrated at reduced pressure to dryness and the solids suspended and washed 5× in 2 volumes of toluene and then filtered and dried.

EXAMPLE 10

Synthesis of [Mn(Bcyclam)$Cl_2$]

This example also further illustrates the conversion of product of Example 1, after purification, to a useful bleach catalyst.

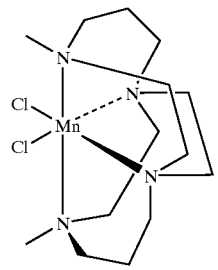

(a) Method I

The "Bcyclam", (5,12-dimethyl-1,5,8,12-tetraaza-bicyclo[6.6.2]hexadecane), is the product of the process of the invention. Bcyclam (1.00 g., 3.93 mmol) is dissolved in dry $CH_3CN$ (35 mL, distilled from $CaH_2$). The solution is then evacuated at 15 mm until the $CH_3CN$ begins to boil. The flask is then brought to atmospheric pressure with Ar. This degassing procedure is repeated 4 times. Mn(pyridine)$_2Cl_2$ (1.12 g., 3.93 mmol), synthesized according to the literature procedure of H. T. Witteveen et al., *J. Inorg. Nucl. Chem.*, (1974), 36, 1535, is added under Ar. The cloudy reaction solution slowly begins to darken. After stirring overnight at room temperature, the reaction solution becomes dark brown with suspended fine particulates. The reaction solution is filtered with a 0.2μ filter. The filtrate is a light tan color. This filtrate is evaporated to dryness using a rotoevaporator. After drying overnight at 0.05 mm at room temperature, 1.35 g. off-white solid product is collected, 90% yield. Elemental Analysis: %Mn, 14.45; %C, 44.22; %H, 7.95; theoretical for [Mn(Bcyclam)Cl$_2$], MnC$_{14}$H$_{30}$N$_4$Cl$_2$, MW=380.26. Found: %Mn, 14.98; %C, 44.48; %H, 7.86; Ion Spray Mass Spectroscopy shows one major peak at 354 mu corresponding to [Mn(Bcyclam)(formate)]$^+$.

(b) Method II (Present Invention Process)

Freshly distilled Bcyclam (25.00 g., 0.0984 mol), which is the product of the present process, is dissolved in dry CH$_3$CN (900 mL, distilled from CaH$_2$). The solution is then evacuated at 15 mm until the CH$_3$CN begins to boil. The flask is then brought to atmospheric pressure with Ar. This degassing procedure is repeated 4 times. MnCl$_2$ (11.25 g., 0.0894 mol) is added under Ar. The cloudy reaction solution immediately darkens. After stirring 4 hrs. under reflux, the reaction solution becomes dark brown with suspended fine particulates. The reaction solution is, if desired, filtered through a 0.2μ filter under dry conditions. The filtrate is a light tan color. This filtrate is evaporated to dryness using a rotoevaporator. The resulting tan solid is dried overnight at 0.05 mm at room temperature. The solid is suspended in toluene (100 mL) and heated to reflux. The toluene is decanted off and the procedure is repeated with another 100 mL of toluene. The balance of the toluene is removed using a rotoevaporator. After drying overnight at 0.05 mm at room temperature, 31.75 g. of a light blue solid product is collected, 93.5% yield. Elemental Analysis: %Mn, 14.45; %C, 44.22; %H, 7.95; %N, 14.73; %Cl, 18.65; theoretical for [Mn(Bcyclam)Cl$_2$], MnC$_{14}$H$_{30}$N$_4$Cl$_2$, MW=380.26. Found: %Mn, 14.69; %C, 44.69; %H, 7.99; %N, 14.78; %Cl, 18.90 (Karl Fischer Water, 0.68%). Ion Spray Mass Spectroscopy shows one major peak at 354 mu corresponding to [Mn(Bcyclam)(formate)]$^+$.

EXAMPLE 11

Synthesis of [Mn(C$_4$-Bcyclam)Cl$_2$] where C$_4$-Bcyclam=5-n-butyl-12-methyl-1,5,8,12-tetraaza-bicyclo[6.6.2]hexadecane

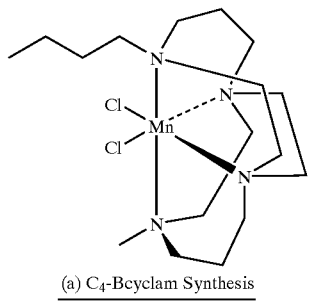

(a) C$_4$-Bcyclam Synthesis

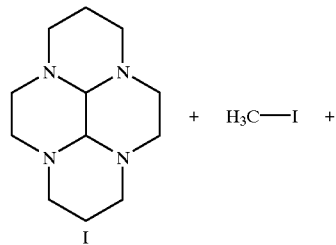

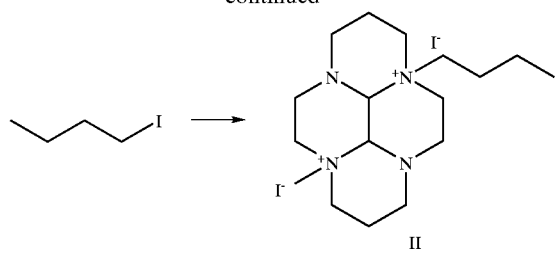

The following synthesis method is conventional and is included for comparative purposes; however the product, (III) (see hereinafter) is another macrocycle which can be manufactured by the hereinabove-described process of the present invention, simply by addition of an additional alkyl halide, 1-iodobutane, to step (B) of the instant process. Tetracyclic adduct (I) can be made using step (A) of the instant process, or, for comparison, can be prepared by the literature method of H. Yamamoto and K. Maruoka, *J. Amer. Chem. Soc.,* (1981) ,103, 4194. I (3.00 g., 13.5 mmol) is dissolved in dry CH$_3$CN (50 mL, distilled from CaH$_2$). 1-Iodobutane (24.84 g., 135 mmol) is added to the stirred solution under Ar. The solution is stirred at room temperature for 5 days. 4-Iodobutane (12.42 g., 67.5 mmol) is added and the solution is stirred an additional 5 days at RT. Under these conditions, I is fully mono-alkylated with 1-iodobutane as shown by $^{13}$C-NMR. Methyl iodide (26.5 g, 187 mmol) is added and the solution is stirred at room temperature for an additional 5 days. The reaction is filtered using Whatman #4 paper and vacuum filtration. A white solid, II, is collected (6.05 g., 82%).

$^{13}$C NMR (CDCl$_3$) 16.3, 21.3, 21.6, 22.5, 25.8, 49.2, 49.4, 50.1, 51.4, 52.6, 53.9, 54.1, 62.3, 63.5, 67.9, 79.1, 79.2 ppm. Electro spray Mass Spec. (MH$^+$/2, 147).

II (6.00 g., 11.0 mmol) is dissolved in 95% ethanol (500 mL). Sodium borohydride (11.0 g., 290 mmol) is added and the reaction turns milky white. The reaction is stirred under Ar for three days. Hydrochloric acid (100 mL, concentrated) is slowly dripped into the reaction mixture over 1 hour. The reaction mixture is evaporated to dryness using a rotoevaporator. The white residue is dissolved in sodium hydroxide (500 mL, 1.00N). This solution is extracted with toluene (2×150 mL). The toluene layers are combined and dried with sodium sulfate. After removal of the sodium sulfate using filtration, the toluene is evaporated to dryness using a rotoevaporator. The resulting oil is dried at room temperature under high vacuum (0.05 mm) overnight. A colorless oil results 2.95 g., 90%. This oil (2.10 g.) is distilled using a short path distillation apparatus (still head temperature 115 C. at 0.05 mm). Yield: 2.00 g. $^{13}$C NMR (CDCl$_3$) 14.0, 20.6, 27.2, 27.7, 30.5, 32.5, 51.2, 51.4, 54.1, 54.7, 55.1, 55.8, 56.1, 56.5, 57.9, 58.0, 59.9 ppm. Mass Spec. (MH$^+$, 297).

(b) [Mn(C$_4$-Bcyclam)Cl$_2$] Synthesis (According to the Present Invention)

C$_4$-Bcyclam (2.00 g., 6.76 mmol) is slurried in dry CH$_3$CN (75 mL, distilled from CaH$_2$). The solution is then evacuated at 15 mm until the CH$_3$CN begins to boil. The flask is then brought to atmospheric pressure with Ar. This degassing procedure is repeated 4 times. MnCl$_2$ (0.81 g., 6.43 mmol) is added under Ar. The tan, cloudy reaction solution immediately darkens. After stirring 4 hrs. under reflux, the reaction solution becomes dark brown with suspended fine particulates. The reaction solution is filtered through a 0.2μ membrane filter under dry conditions. The filtrate is a light tan color. This filtrate is evaporated to dryness using a rotoevaporator. The resulting white solid is suspended in toluene (50 mL) and heated to reflux. The toluene is decanted off and the procedure is repeated with another 100 mL of toluene. The balance of the toluene is removed using a rotoevaporator. After drying overnight at 0.05 mm, RT, 2.4 g. a light blue solid (III) results, 88% yield. Ion Spray Mass Spectroscopy shows one major peak at 396 mu corresponding to [Mn($C_4$-Bcyclam)(formate)]$^+$.

EXAMPLE 12

Synthesis of [Mn(Bz-Bcyclam)$Cl_2$] where Bz-Bcyclam=5-benzyl-12-methyl-1,5,8,12-tetraaza-bicyclo[6.6.2]hexadecane (a) Bz-Bcyclam Synthesis

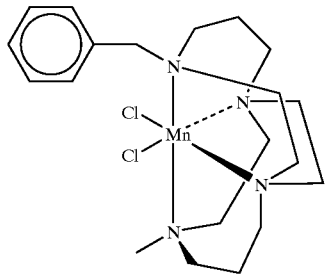

The macrocycle is synthesized similarly to the $C_4$-Bcyclam synthesis described above, except that benzyl bromide is used in place of the 1-iodobutane in step (B) of the instant process. $^{13}$C NMR (CDCl$_3$) 27.6, 28.4, 43.0, 52.1, 52.2, 54.4, 55.6, 56.4, 56.5, 56.9, 57.3, 57.8, 60.2, 60.3, 126.7, 128.0, 129.1, 141.0 ppm. Mass Spec. (MH$^+$, 331).

(b) [Mn(Bz-Bcyclam)$Cl_2$] Synthesis

This complex is made similarly to the [Mn($C_4$-Bcyclam)$Cl_2$] synthesis described above except that Bz-Bcyclam is used in place of the $C_4$-Bcyclam. Ion Spray Mass Spectroscopy shows one major peak at 430 mu corresponding to [Mn(Bz-Bcyclam)(formate)]$^+$.

EXAMPLE 13

Synthesis of [Mn($C_8$-Bcyclam)$Cl_2$ were $C_8$-Bcyclam=5-n-octyl-12-methyl-1,5,8,12-tetraaza-bicyclo[6.6.2]hexadecane (a) $C_8$-Bcyclam Synthesis:

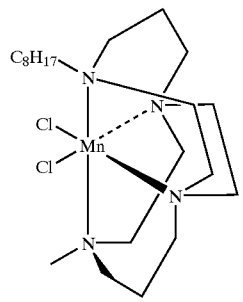

This ligand is synthesized similarly to the $C_4$-Bcyclam synthesis described above except that 1-iodooctane is used in place of the 1-iodobutane.

Mass Spec. (MH$^+$, 353).

(b) [Mn($C_8$-Bcyclam)$Cl_2$] Synthesis

This complex is made similarly to the [Mn($C_4$-Bcyclam)$Cl_2$] synthesis described above except that $C_8$-Bcyclam is used in place of the $C_4$-Bcyclam.

Ion Spray Mass Spectroscopy shows one major peak at 452 mu corresponding to [Mn($B_8$-Bcyclam)(formate)]$^+$.

EXAMPLE 14

Synthesis of [Mn($H_2$-Bcyclam)$Cl_2$] where $H_2$-Bcyclam=1,5,8,12-tetraaza-bicyclo[6.6.2] hexadecane

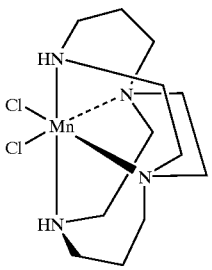

The $H_2$-Bcyclam is synthesized similarly to the $C_4$-Bcyclam synthesis described above except that benzyl bromide is used in place of the 1-iodobutane and the methyl iodide. The benzyl groups are removed by catalytic hydrogenation. Thus, the resulting 5,12-dibenzyl-1,5,8,12-tetraaza-bicyclo[6.6.2]hexadecane and 10% Pd on charcoal is dissolved in 85% acetic acid. This solution is stirred 3 days at room temperature under 1 atm. of hydrogen gas. The solution is filtered though a 0.2 micron filter under vacuum. After evaporation of solvent using a rotary evaporator, the product is obtained as a colorless oil. Yield: 90$^+$%.

The Mn complex is made similarly to the [Mn(Bcyclam)$Cl_2$] synthesis described hereinabove except that the that $H_2$-Bcyclam is used in place of the Bcyclam.

Elemental Analysis: %C, 40.92; %H, 7.44; %N, 15.91; theoretical for [Mn($H_2$-Bcyclam)$Cl_2$], MnC$_{12}$H$_{26}$N$_4$Cl$_2$, MW=352.2. Found: %C, 41.00; %H, 7.60; %N, 15.80. FAB+ Mass Spectroscopy shows one major peak at 317 mu corresponding to [Mn($H_2$-Bcyclam)Cl]$^+$ and another minor peak at 352 mu corresponding to [Mn($H_2$-Bcyclam)$Cl_2$]$^+$.

EXAMPLE 15

Synthesis of [Fe($H_2$-Bcyclam)$Cl_2$] where $H_2$-Bcyclam=1,5,8,12-tetraaza-bicyclo[6.6.21] hexadecane

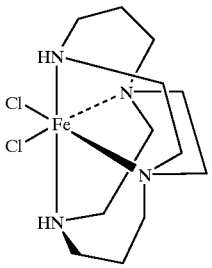

The Fe complex is made similarly to the [Mn($H_2$-Bcyclam)$Cl_2$] synthesis described hereinabove except that the that anhydrous FeCl$_2$ is used in place of the MnCl$_2$.

Elemental Analysis: %C, 40.82; %H, 7.42; %N, 15.87; theoretical for [Fe($H_2$-Bcyclam)$Cl_2$], FeC$_{12}$H$_{26}$N$_4$Cl$_2$, MW=353.1. Found: %C, 39.29; %H, 7.49; %N, 15.00. FAB+ Mass Spectroscopy shows one major peak at 318 mu corresponding to [Fe(H$_2$-Bcyclam)Cl]$^+$ and another minor peak at 353 mu corresponding to [Fe(H$_2$-Bcyclam)Cl$_2$]$^+$.

EXAMPLE 16

Synthesis of:

Chloro-20-methyl-1,9,20,24,25-pentaaza-tetracyclo [7.7.7.1$^{3,7}$.1$^{11,15}$.]pentacosa-3,5,7(24),11,13,15(25)-hexaene manganese(II) hexafluorophosphate ,7(b); Trifluoromethanesulfono-20-methyl-1,9,20,24,25-pentaaza tetracyclo[7.7.7.1$^{3,7}$.1$^{11,15}$.]pentacosa-3,5,7(24),11,13,15 (25)-hexaene manganese(II) trifluoromethanesulfonate, 7(c) and Thiocyanato-20-methyl-1,9,20,24,25-pentaaza-tetracyclo[7.7.7.1$^{3,7}$.1$^{11,15}$.]pentacosa-3,5,7(24),11,13,15 (25)-hexaene iron(II) thiocyanate, 7(d)

(a) Synthesis of the Ligand 20-methyl-1,9,20,24,25-pentaaza-tetracyclo [7.7.7.1$^{3,7}$.1$^{11,15}$.]pentacosa-3,5,7(24),11,13,15(25)-hexaene The ligand 7-methyl-3,7,11,17-tetraazabicyclo11.3.1$^{17}$] heptadeca-1(17), 13, 15-triene is synthesized by the literature procedure of K. P. Balakrishnan et al., *J. Chem. Soc., Dalton Trans.,* 1990, 2965.

7-methyl-3,7,11,17-tetraazabicyclo[11.3.1 $^{17}$]heptadeca-1 (17), 13, 15-triene (1.49 g, 6 mmol) and O,O'-bis (methanesulfonate)-2,6-pyridine dimethanol (1.77 g, 6 mmol) are separately dissolved in acetonitrile (60 ml). They are then added via a syringe pump (at a rate of 1.2 ml/hour) to a suspension of anhydrous sodium carbonate (53 g, 0.5 mol) in acetonitrile (1380 ml). The temperature of the reaction is maintained at 65° C. throughout the total reaction of 60 hours.

After cooling, the solvent is removed under reduced pressure and the residue is dissolved in sodium hydroxide solution (200 ml, 4M). The product is then extracted with benzene (6 times 100 ml) and the combined organic extracts are dried over anhydrous sodium sulfate. After filtration the solvent is removed under reduced pressure. The product is then dissolved in an acetonitrile/triethylamine mixture (95:5) and is passed through a column of neutral alumina (2.5×12 cm). Removal of the solvent yields a white solid (0.93 g, 44%).

This product may be further purified by recrystallization from an ethanol/diethylether mixture combined with cooling at 0° C. overnight to yield a white crystalline solid. Anal. Calcd. for C$_{21}$H$_{29}$N$_5$: C, 71.75; H, 8.32; N, 19.93. Found: C, 71.41; H, 8.00; N, 20.00. A mass spectrum displays the expected molecular ion peak [for C$_{21}$H$_{30}$N$_5$]$^+$ at m/z=352. The $^1$H NMR(400 MHz, in CD$_3$CN) spectrum exhibits peaks at δ=1.81 (m,4H); 2.19 (s, 3H); 2.56 (t, 4H); 3.52 (t,4H); 3.68 (AB, 4H), 4.13 (AB, 4H), 6.53 (d, 4H) and 7.07 (t, 2H). The $^{13}$C NMR(75.6 MHz, in CD$_3$CN) spectrum shows eight peaks at δ=24.05, 58.52, 60.95, 62.94, 121.5, 137.44 and 159.33 ppm.

All metal complexation reactions are performed in an inert atmosphere glovebox using distilled and degassed solvents.

(b) Complexation of the Ligand L$_1$ with Bis(Pyridine) Manganese (II) Chloride

Bis(pyridine)manganese (II) chloride is synthesized according to the literature procedure of H. T. Witteveen et al., *J. Inorg. Nucl. Chem.,* 1974, 36, 1535.

The ligand L$_1$ (1.24 g, 3.5 mmol), triethylamine(0.35 g, 3.5 mmol) and sodium hexafluorophosphate (0.588 g, 3.5 mmol) are dissolved in pyridine (12 ml). To this is added bis(pyridine)manganese (II) chloride and the reaction is stirred overnight. The reaction is then filtered to remove a white solid. This solid is washed with acetonitrile until the washings are no longer colored and then the combined organic filtrates are evaporated under reduced pressure. The residue is dissolved in the minimum amount of acetonitrile and allowed to evaporate overnight to produce bright red crystals. Yield: 0.8 g (39%). Anal. Calcd. for C$_{21}$H$_{31}$N$_5$Mn$_1$Cl$_1$P$_1$F$_6$: C, 43.00; H, 4.99 and N, 11.95. Found: C, 42.88; H, 4.80 and N 11.86. A mass spectrum displays the expected molecular ion peak [for C$_{21}$H$_{31}$N$_5$Mn$_1$Cl$_1$] at m/z=441. The electronic spectrum of a dilute solution in water exhibits two absorption bands at 260 and 414 nm (ε=1.47×10$^3$ and 773 M$^{-1}$ cm$^{-1}$ respectively). The IR spectrum (KBr) of the complex shows a band at 1600 cm$^{-1}$ (pyridine), and strong bands at 840 and 558 cm$^{-1}$ (PF$_6^-$).

(c) Complexation of the Ligand with Manganese (II) Trifluoromethanesulfonate

Manganese (II) trifluoromethanesulfonate is prepared by the literature procedure of Bryan and Dabrowiak, Inorg. Chem., 1975, 14, 297.

Manganese (II) trifluoromethanesulfonate (0.883 g, 2.5 mmol) is dissolved in acetonitrile (5 ml). This is added to a solution of the ligand L$_1$ (0.878 g, 2.5 mmol) and triethylamine (0.25 g, 2.5 mmol) in acetonitrile (5 ml). This is then heated for two hours before filtering and then after cooling removal of the solvent under reduced pressure. The residue is dissolved in a minimum amount of acetonitrile and left to evaporate slowly to yield orange crystals. Yield 1.06 g (60%). Anal. Calc. for Mn$_1$C$_{23}$H$_{29}$N$_5$S$_2$F$_6$O$_6$: C, 39.20; H, 4.15 and N, 9.95. Found: C, 38.83; H, 4.35 and N, 10.10. The mass spectrum displays the expected peak for [Mn$_1$C$_{22}$H$_{29}$N$_5$S$_1$F$_3$O$_3$]$^+$ at m/z=555. The electronic spectrum of a dilute solution in water exhibits two absorption bands at 260 and 412 nm (ε=9733 and 607 M$^{-1}$cm$^{-1}$ respectively). The IR spectrum (KBr) of the complex shows a band at 1600 cm$^{-1}$ (pyridine) and 1260, 1160 and 1030cm$^{-1}$ (CF$_3$SO$_3$).

(d) Complexation of the Ligand with Iron (II) Trifluoromethanesulfonate

Iron (II) trifluoromethanesulfonate is prepared in situ by the literature procedure Tait and Busch, *Inorg. Synth.,* 1978, XVIII, 7.

The ligand (0.833 g, 2.5 mmol) and triethylamine (0.505 g, 5 mmol) are dissolved in acetonitrile (5 ml). To this is added a solution of hexakis(acetonitrile) iron (II) trifluoromethanesulfonate (1.5 g, 2.5 mmol) in acetonitrile (5 ml) to yield a dark red solution. Sodium thiocyanate (0.406 g, 5 mmol) is then added and the reaction stirred for a further hour. The solvent is then removed under reduced pressure and the resulting solid is recrystallized from methanol to produce red microcrystals. Yield: 0.65 g (50%). Anal. Calc. for Fe$_1$C$_{23}$H$_{29}$N$_7$S$_2$:C, 52.76; H, 5.59 and N, 18.74. Found: C 52.96; H, 5.53; N, 18.55. A mass spectrum displays the expected molecular ion peak [for Fe$_1$C$_{22}$H$_{29}$N$_6$S$_1$]$^+$ at m/z= 465. The $^1$H NMR (300 MHz, CD$_3$CN)δ1.70(AB,2H), 2.0 (AB,2H), 2.24 (s,3H), 2.39 (m,2H), 2.70 (m,4H), 3.68 (m,4H), 3.95 (m,4H), 4.2 (AB, 2H), 7.09 (d,2H), 7.19 (d,2H), 7.52 (t,1H), 7.61 (d,1H). The IR spectrum (KBr) of the spectrum shows peaks at 1608 cm$^{-1}$ (pyridine) and strong peaks at 2099 and 2037 cm$^{-1}$(SCN$^-$).

The metal complexes can be used in detergents, for example by adding about 0.05% of complex to a granular detergent containing 10% sodium perborate, to improve bleaching.

Purification of Catalyst

In general, the state of purity of the transition-metal oxidation catalyst of Example 9 can vary, provided that any impurities, such as byproducts of the synthesis, free ligand (s), unreacted transition-metal salt precursors, colloidal organic or inorganic particles, and the like, are not present in amounts which substantially decrease the utility of the transition-metal oxidation catalyst. It has been discovered to be desirable that the transition-metal oxidation catalyst should be purified. This can be done using any suitable means, such that the catalyst does not excessively consume available oxygen (AvO). Excessive AvO consumption is defined as including any instance of exponential decrease in AvO levels of bleaching, oxidizing or catalyzing solutions with time at 20–40° C. Preferred transition-metal oxidation catalysts, whether purified or not, when placed into dilute aqueous buffered alkaline solution at a pH of about 9 (carbonate/bicarbonate buffer) at temperatures of about 40° C., have a relatively steady decrease in AvO levels with time; in preferred cases, this rate of decrease is linear or approximately linear. In the preferred embodiments, there is a rate of AvO consumption at 40 deg C. given by a slope of a graph of % AvO vs. time (in sec.) (hereinafter "AvO slope") of from about −0.0050 to about −0.0500, more preferably −0.0100 to about −0.0200. Thus, a preferred Mn(II) oxidation catalyst has an AvO slope of from about −4.0140 to about −0.0182; in contrast, a somewhat less preferred transition metal oxidation catalyst has an AvO slope of −0.0286.

Preferred methods for determining AvO consumption in aqueous solutions of transition metal oxidation catalysts herein include the well-known iodometric method or its variants, such as methods commonly applied for hydrogen peroxide. See, for example, Organic Peroxides, Vol. 2., D. Swern (Ed.,), Wiley-Interscience, New York, 1971, for example the table at p. 585 and references therein including P. D. Bartlett and R. Altscul, J. Amer. Chem. Soc., 67, 812 (1945) and W. E. Cass, J. Amer. Chem. Soc., 68, 1976 (1946). Accelerators such as ammonium molybdate can be used. The general procedure used herein is to prepare an aqueous solution of catalyst and hydrogen peroxide in a mild alkaline buffer, for example carbonate/bicarbonate at pH 9, and to monitor the consumption of hydrogen peroxide by periodic removal of aliquots of the solution which are "stopped" from further loss of hydrogen peroxide by acidification using glacial acetic acid, preferably with chilling (ice). These aliquots can then be analyzed by reaction with potassium iodide, optionally but sometimes preferably using ammonium molybdate (especially low-impurity molybdate, see for example U.S. Pat. No. 4,596,701) to accelerate complete reaction, followed by back-titratation using sodium thiosulfate. Other variations of analytical procedure can be used, such as thermometric procedures, potential buffer methods (Ishibashi et al., Anal. Chim. Acta (1992), 261(1–2), 405–10) or photometric procedures for determination of hydrogen peroxide (EP 485,000 A2, May 13, 1992). Variations of methods permitting fractional determinations, for example of peracetic acid and hydrogen peroxide, in presence or absence of the instant transition-metal oxidation catalysts are also useful; see, for example JP 92-303215, Oct. 16, 1992.

In another embodiment of the present invention, there are encompassed laundry and cleaning compositions incorporating transition-metal oxidation catalysts which have been purified to the extent of having a differential AvO loss reduction, relative to the untreated catalyst, of at least about 10% (units here are dimensionless since they represent the ratio of the AvO slope of the treated transition-metal oxidation catalyst over the AvO slope for the untreated transition metal oxidation catalyst—effectively a ratio of AvO's).

In other terms, the AvO slope is improved by purification so as to bring it into the above-identified preferred ranges.

In yet another embodiment of the instant invention, two processes have been identified which are particularly effective in improving the suitability of transition-metal oxidation catalysts, as synthesized, for incorporation into laundry and cleaning products or for other useful oxidation catalysis applications.

One such process is any process having a step of treating the transition-metal oxidation catalyst, as prepared, by extracting the transition-metal oxidation catalyst, in solid form, with an aromatic hydrocarbon solvent; suitable solvents are oxidation-stable under conditions of use and include benzene and toluene, preferably toluene. Surprisingly, toluene extraction can measurably improve the AvO slope (see disclosure hereinabove).

Another process which can be used to improve the AvO slope of the transition metal oxidation catalyst is to filter a solution thereof using any suitable filtration means for removing small or colloidal particles. Such means include the use of fine-pore filters; centrifugation; or coagulation of the colloidal solids.

In more detail, a full procedure for purifying a transition-metal oxidation catalyst herein can include:

(a) dissolving the transition-metal oxidation catalyst, as prepared, in hot acetonitrile:

(b) filtering the resulting solution hot, e.g., at about 70° C., through glass microfibers (for example glass microfiber filter paper available from Whatman);

(c) if desired, filtering the solution of the first filtration through a 0.2 micron membrane, (for example, a 0.2 micron filter commercially available from Millipore), or centrifuging, whereby colloidal particles are removed;

(d) evaporating the solution of the second filtration to dryness;

(e) washing the solids of step (d) with toluene, for example five times using toluene in an amount which is double the volume of the oxidation catalyst solids;

(f) drying the product of step (e).

Another procedure which can be used, in any convenient combination with aromatic solvent washes and/or removal of fine particles is recrystallization. Recrystallization, for example of Mn(II) Bcyclam chloride transition-metal oxidation catalyst, can be done from hot acetonitrile. Recrystallization can have its disadvantages, for example it may on occasion be more costly.

What is claimed is:

1. A method for preparing a cross-bridged macropolycycle, said method comprising derivatizing N,N'-bis-(2-aminoethyl)-1,3-propanediamine by a series of steps including:

quaternizing an intermediate using a quaternizing agent, wherein said step is carried out using less than fifteen-fold of said quaternizing agent; and reducing a diquaternized intermediate, wherein said step is carried out using an amount less than fifteen-fold of reducing agent;

and wherein further said series of steps is carried out using one solvent system and in the absence of any step of vacuum distilling an intermediate.

2. A method according to claim 1, carried out at or below 50° C.

3. A method according to claim 1, wherein said quaternization and reduction steps are carried out at the temperatures of from ambient temperature to 50° C.

4. A method for producing a complex of Mn and a cross-bridged macropolycyclic ligand, said method comprising reacting with manganous chloride a cross-bridged macropolycycle prepared in accordance with claim 1.

5. A method for producing a complex of Mn and a cross-bridged macropolycyclic ligand, said method comprising reacting a cross-bridged macropolycycle prepared in accordance with claim 1 with $MnCl_2$ which has been produced by an anhydrous reaction of manganese metal with a chlorinating agent.

6. A method according to claim 4, conducted in a non-aqueous solvent.

7. A method according to claim 5, conducted in a non-aqueous solvent.

* * * * *